United States Patent
Calvert

(10) Patent No.: US 7,125,254 B2
(45) Date of Patent: Oct. 24, 2006

(54) APPARATUS AND METHOD FOR ROOT CANAL OBTURATION

(76) Inventor: Randall Rex Calvert, 5026 157th Ct. NE., Redmond, WA (US) 98052

( * ) Notice: Subject to any disclaimer, the term of this patent is extended or adjusted under 35 U.S.C. 154(b) by 0 days.

(21) Appl. No.: 10/035,544

(22) Filed: Dec. 28, 2001

(65) Prior Publication Data

US 2003/0124482 A1   Jul. 3, 2003

(51) Int. Cl.
*A61C 13/30* (2006.01)

(52) U.S. Cl. .................. 433/224; 433/220; 433/81

(58) Field of Classification Search .............. 433/81, 433/102, 220, 224, 221
See application file for complete search history.

(56) References Cited

U.S. PATENT DOCUMENTS

| | | | | |
|---|---|---|---|---|
| 4,758,156 | A | | 7/1988 | Johnson ................ 433/81 |
| 5,284,443 | A | * | 2/1994 | Weil .................... 433/224 |
| 5,326,263 | A | * | 7/1994 | Weissman ............. 433/224 |
| 5,503,559 | A | * | 4/1996 | Vari .................... 433/224 |
| 5,915,970 | A | * | 6/1999 | Sicurelli, Jr. et al. ..... 433/220 |
| 5,919,044 | A | * | 7/1999 | Sicurelli, Jr. et al. ..... 433/220 |
| 5,989,032 | A | * | 11/1999 | Reynaud et al. ........ 433/224 |
| 6,183,253 | B1 | * | 2/2001 | Billet et al. ............ 433/81 |
| 6,267,597 | B1 | * | 7/2001 | Kim .................... 433/224 |
| 6,353,041 | B1 | | 3/2002 | Qian ................... 523/116 |
| 6,371,763 | B1 | * | 4/2002 | Sicurelli, Jr. et al. ..... 433/220 |
| 6,428,319 | B1 | * | 8/2002 | Lopez et al. ........... 433/224 |
| 6,500,004 | B1 | * | 12/2002 | Jensen et al. .......... 433/228.1 |
| 2003/0113686 | A1 | | 6/2003 | Jia et al. |
| 2003/0124483 | A1 | | 7/2003 | Jia et al. |

FOREIGN PATENT DOCUMENTS

| | | |
|---|---|---|
| DE | 44 13 272 A1 * | 10/1994 |
| DE | 19646037 A1 * | 5/1998 |
| EP | 0938875 A2 * | 9/1999 |
| WO | WO 98/11842 * | 3/1998 |
| WO | WO 2004/037214 A1 | 5/2004 |

OTHER PUBLICATIONS

Light Speed Endodontics, Endodontic Products Catalog, Jan. 2001.
FibreFill™ Endodontic Obturating System, Product Overview, http://63.241.176.151/products/fibrefilloverview.html, p. 1, last accessed Jan. 3, 2002.
FibreKor® Post System, Product Overview, http://63.241.176.151/products/fibrekoroverview.html, pp. 1-2, last accessed Jan. 3, 2001.
Dr. L. Stephen Buchanan—Endodontics, Other Products and Designs, http://www.endobuchanan.com/flowbody.html, pp. 1-6, last accessed Jan. 3, 2002.
Bicso Catalog, Fiber Posts, http://www.bisco.com/catalog/aza_bisco_brandNamef.asp?iCat_Id=8, 10 pages, last accessed Jan. 3, 2002.

* cited by examiner

*Primary Examiner*—Ralph A. Lewis
(74) *Attorney, Agent, or Firm*—Black Lowe & Graham, PLLC

(57) ABSTRACT

The present invention is directed to root canal obturation in a tooth. In one embodiment, a plug is positioned in a root canal and bonded to the root canal by applying a light-curing adhesive to the canal and exposing the plug to a light source to bond the plug to the root canal. In another embodiment, a carrier is disclosed having an optically transmissive plug portion for insertion into the canal. In still another embodiment, the plug portion of the carrier includes an optical fiber to transmit light from a light source into the plug portion. In still yet another embodiment, a filler material is heated and injected into the root canal in a semi-liquid state and exposed to light to cure the adhesive.

44 Claims, 13 Drawing Sheets

APPARATUS AND METHOD FOR ROOT CANAL OBTURATION

TECHNICAL FIELD

The present invention relates to root canal therapy, and more particularly, to an apparatus and method for performing root canal obturation.

BACKGROUND OF THE INVENTION

The root canal procedure is a well-known endodontic therapy for the treatment of pulp necrosis and for the retreatment of previously obturated canals that have failed. The procedure generally includes removing at least a portion of the tooth crown to expose the canal system, followed by the extraction of the contents from the one or more canals of the tooth. The canals are then generally subjected to mechanical shaping operations, such as reaming or filing in order to reduce and/or remove various irregularities within the canal, and to prepare the canal to receive a filling material. While the canals are shaped, the canals are regularly cleaned with a variety of solutions to remove material dislodged by the shaping operations, and to prepare the canals to receive a filling material. The filling material is generally tightly packed into the canals to form a seal within the canals to prevent leakage into the canal spaces. An additional filling material is then generally placed in the crown opening. Alternatively, a replacement crown may be affixed to the tooth to complete the procedure.

In most instances, complete obturation of the canals is complicated by the internal shape of the canals. The canals are generally curved, and often have an irregular cross sectional area along the length of the canal. Additionally, the canals frequently have lateral fissures, or passages, that radiate outwardly from the interior of the canal. Accordingly, the filling material and the method used to obturate the canals must be capable of adequately conforming to the curved and/or irregular shape of the canals, and to substantially fill and seal the canals, including the lateral fissures, if the therapy is to be successful.

One prior art endodontic technique employs silver points in conjunction with a sealer to obturate the canal passage. The silver point is a relatively slender and slightly tapered metal insert that, when properly positioned in the canal, extends to the foramen at the apical tip of the root. Since the silver point generally has a diameter that is much less than the diameter of the canal, the sealer is employed solely to fill the space between the silver point and the interior surface of the canal. The sealer is a relatively viscous semi-fluid material that does not chemically interact with either the silver point or the tooth material and does not form an adhesive bond with the silver point or the surrounding tooth material. Instead, the sealer serves as an interface material between the canal wall and the silver point to prevent the migration of liquid substances along the interface region between the tooth and the silver point.

Although the silver point technique is relatively simple and may be relatively quickly administered, a principal disadvantage is that the silver point does not adequately "cork" the apical foramen to create the desired seal. Further, the technique generally cannot subject the relatively viscous sealer material to sufficient hydrostatic pressure to ensure that all of the irregular spaces and lateral fissures in the interface region are sufficiently filled, since the sealer is generally incapable of adequately migrating into either the irregular spaces, or the minute lateral fissures or accessory canals that radiate outwardly from the root canal passage. Consequently, the use of silver points in root canal therapy exhibits a relatively high degree of failure, which often necessitates the retreatment of the affected tooth.

Various other prior art endodontic techniques use an elastic material, called gutta percha, as the filling material. Gutta percha is a natural rubber material that is semi-rigid at room temperatures that becomes plastic, or semi-liquid upon heating. The gutta percha material is generally formed into relatively long and slender tapered points that may be introduced into the root canal by either a vertical condensation or a lateral condensation method.

In the vertical condensation method, the gutta percha point is introduced into the canal with a relatively viscous sealer applied to the inner surfaces of the canal. The point is heated and a relatively small amount of gutta percha is removed from the canal leaving a softened portion of gutta percha within the canal. This portion is subjected to vertical compression by a tool called a plugger to form a relatively densely compressed mass within the canal of the tooth. The process of heating the point, removing a small portion, and condensing the remaining portion is repeated two or more times. This technique thus subjects the gutta percha material to significant hydrostatic pressure, which forces the sealer and the softened gutta percha into the small irregularities and accessory canals found within the root. The condensing process is complete when the apical three to five millimeters of the canal is sealed with thermally softened gutta percha that conforms to the irregular shape of the canal. The next step is to "back fill" the remaining unfilled portion of the canal. One common method to accomplish the backfilling procedure is to inject warm gutta percha material into the canal with a "gutta percha gun" such as the Obtura II system, available from Spartan/Obtura Inc. of Fenton, Mo. According to this method, a gutta percha pellet is inserted into the gun and heated to a predetermined temperature. The thermally softened gutta percha is expressed in small increments into the canal through a narrow tip of the gun starting at the most recently condensed portion of gutta percha. Vertical condensation then proceeds by compressing the material with the plugger to compact the gutta percha while it is cooling. The process of expressing a small amount of gutta percha into the canal followed by vertical compaction is repeated until the canal is filled to the desired length.

An alternative method for obturating the canal space that entails fewer steps and less equipment than the foregoing method is to utilize a commercially-available gutta percha carrier unit. The unit comprises an elongated, axisymmetric plastic portion having a small handle at one end, and a mass of gutta percha disposed on an opposing end that extends along a portion of the length of the plastic portion. In this method, the operator places a sealer into the canal and, while holding the handle of the unit, heats the gutta percha on the carrier to soften it. The gutta percha disposed on the unit is then introduced into the canal. The portion of the carrier protruding from the tooth is then removed and the root canal procedure is complete.

In the lateral condensation method, a main gutta percha point is introduced into the root canal, followed by the successive introduction of additional points surrounding the main point until the root canal is completely filled. As in vertical condensation, a sealer is used to provide a relatively fluid impermeable interface between the tooth and the gutta percha material.

Although the foregoing techniques constitute a substantial improvement over the silver point technique, numerous drawbacks still exist. For example, the introduction of gutta percha points into the canal, either by the vertical or lateral condensation methods discussed above, is generally time consuming, and requires a high degree of skill to ensure that the therapy is successful. For example, in the vertical condensation method, the force applied to the material must be sufficient to create sufficient hydrostatic force to compress the gutta percha and sealer into all of the internal spaces in the canal. However, the application of excessive force to the gutta percha may cause the tooth to be inadvertently fractured, or otherwise damaged. In addition, the application of excessive force to the gutta percha material may cause the material, or the sealer to be extruded through the apical foramen and into the surrounding tissue to form an impacted mass of material that may lead to localized irritation, or even inflammation of the periapical tissue. Still further, the viscous sealer employed is generally unable to fully migrate into minute fissures, or to chemically bond with the tooth or the filler material, as discussed above.

Although using the gutta percha carrier unit, as discussed more fully above, has greatly simplified the process of obturating the root canal, there are additional drawbacks associated with this method. With the vertical or lateral condensation techniques, the main or master cone can be trimmed to size or chemically softened for proper seating and then radiographed while lodged in the canal to verify that the canal is properly filled. This pre-fitting procedure is accomplished prior to the actual obturation process, but cannot be performed with the carrier technique. Consequently, the operator usually has a single opportunity to heat the gutta percha on the carrier and insert it into the canal in an attempt to properly seat the gutta percha to the desired length. Further, when retreatment of a root canal is required where the canal has been previously obturated with a carrier unit, the retreatment is more difficult due to the presence of the plastic carrier, which causes the material to be more difficult to remove, since the carrier unit may not dissolve in any of the conventional solvents typically used to remove root canal filling materials. Accordingly, a significant amount of time may be expended by the operator in removing and repairing the failed treatment.

Although the use of gutta percha has greatly improved the success rate of endodontic treatment, this success relies on the ability of gutta percha to mechanically "plug" the various openings of the canal, since the sealer does not provide bonding or chemo-mechanical adherence between the tooth material and the gutta percha material.

Chemical bonding agents have been successfully used in general dentistry for a number of years to bond composite and porcelain restorations onto and into teeth. Studies have shown that when such bonding agents are used as filling materials to seal the coronal portion of canals filled with gutta percha, the bonded area is impervious to leakage. Accordingly, there is a need in the art for an apparatus and method for obturating the canal utilizing a similar bonding agent that will greatly improve the seal of the canal while generally reducing the time and the relatively high degree of skill required to perform the procedure.

SUMMARY OF THE INVENTION

The present invention is directed to an apparatus and method for obturating a canal in a tooth. In one aspect of the present invention, a plug is provided that may be positioned in a canal of a tooth. The plug is similar in size, shape and flexibility to the currently available gutta percha and with which dentists are familiar. The plug is optically transparent or translucent. The canal is sealed by placing a light-cured or dual-cured adhesive and/or composite into the canal prior to the insertion of the plug. The plug is exposed to a light source to transmit the light into the canal causing the adhesive to set.

In another aspect of the present invention, a carrier having an optically translucent or transparent plug portion is disclosed. An adhesive is introduced into the canal prior to the introduction of the carrier into the canal. A light source is used to cure the adhesive.

In still another aspect of the invention, a carrier having an optically transparent or translucent plug portion is disclosed. The plug portion includes an optical fiber that extends through the plug portion to transmit light from a light source into the canal.

In still yet another aspect of the invention, a plug, or alternatively, a carrier that includes a plug portion is disclosed that includes a phosphorescent material that is exposed to light prior to insertion into the canal. The light-charged plug or plug portion is inserted into the canal and exposed to a light source to cure the adhesive.

In still another aspect, a plug, or alternatively, a carrier that includes a plug portion is disclosed that includes a radioactive isotope that has a relatively-short half-life. The radioactive emissions from the plug or plug portion activates the adhesive to set once the plug or plug portion is positioned in the canal.

In still another aspect, a plug, or alternatively, a carrier that includes a plug portion is disclosed that includes a base part of a two part bonding system. A catalyst is then applied to the canal to bond the plug or plug portion to the canal. Alternatively, the plug or plug portion is formulated to be the catalyst, and a base compound is applied to the canal.

In still another aspect, small particles are formed of an optically transparent or translucent material similar in size and shape as the currently available gutta percha particles that are inserted in to a gutta percha gun for placement of the optically transparent or translucent material into the canal.

DETAILED DESCRIPTION OF THE INVENTION

The present invention is generally directed to root canal therapy. More particularly, the invention relates to a method and apparatus for root canal obturation. Many of the specific details of certain embodiments of the invention are set forth in the following description and in FIGS. 1 through 17 to provide a thorough understanding of such embodiments. One skilled in the art will understand, however, that the present invention may be practiced without several of the details described in the following description. Furthermore, in the following description, an optically transmissive material will be understood to refer to an optically transparent or an optically translucent material. An optically transparent material will be understood to refer to a material that is capable of transmitting at least a portion of the incident radiation applied to the material, and an optically translucent material will be understood to refer to a material that is capable of transmitting at least a portion of the incident radiation applied to the material, while simultaneously diffusing the radiation as it passes through the material. Still further, unless otherwise indicated, the terms transparent and translucent are not to be interpreted as wavelength dependent properties of the materials. Moreover, in the description that follows, it is understood that the figures related to the various embodiments are not to be interpreted as conveying any specific or relative physical dimension, and that specific or relative dimensions related to the various embodiments, if stated, are not to be considered limiting unless the claims expressly state otherwise.

Figure 1:
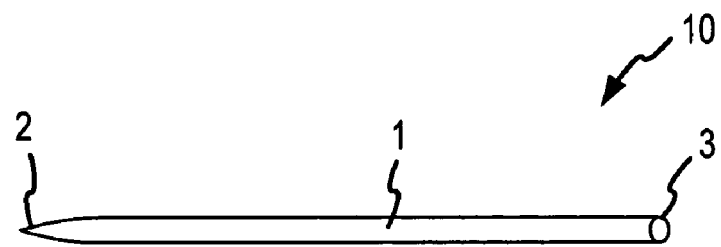
FIG. 1 is a plan view of a plug for root canal obturation according to an embodiment of the invention.

FIG. 1 is a plan view of a plug 10 for root canal obturation according to an embodiment of the invention. The plug 10 is comprised of an elongated body 1 having a distal end 2 and a proximal end 3 that may taper from the proximal end 3 towards the distal end 2 so that the plug 10 may be positioned within the generally tapered root canal of a tooth with the distal end 2 adjacent to an apical portion of the tooth. The plug 10 may further be suitably proportioned to fill the root canal in the tooth by providing a range of sizes that are selectable by an endodontist. For example, the plug 10 may be manufactured in standardized sizes or feather tip sizes, or sizes customized to fit a predetermined taper of currently available endodontic rotary instruments that vary in overall length, width, degree of taper, or any combination of length, width and taper, in order to more closely adapt to the generally unique features of a given root canal. The plug 10 may be formed from any flexible and resilient polymer material that is optically transparent or optically translucent and suitable for biological implantation. For example, the plug 10 may be comprised of silicones, polyethylenes, polyurethanes, polytetraflouroethylenes, polymethylmethacrylates (PMMA) and polytetraflourethyenes (PTFE) among other materials. The plug 10 may also include compounds that augment the opacity of the plug 10 when the plug 10 is subjected to radiographic examination. Accordingly, radio-opacifiers comprised of compounds of barium or bismuth may be used, although other suitable radio-opacifiers are known in the art. The plug 10 is formulated to be generally compatible with numerous light-curing adhesive compounds to allow the plug 10 to be chemically bonded to an interior surface of a root canal upon exposure of the plug 10 to a light source. Accordingly, the light-curing adhesive may include acrylics, cyanoacrylates, and silicones that are light curing, although other compounds may also be used. Bonding the plug 10 to the interior surface of the root canal will be discussed in greater detail below.

Figure 2:
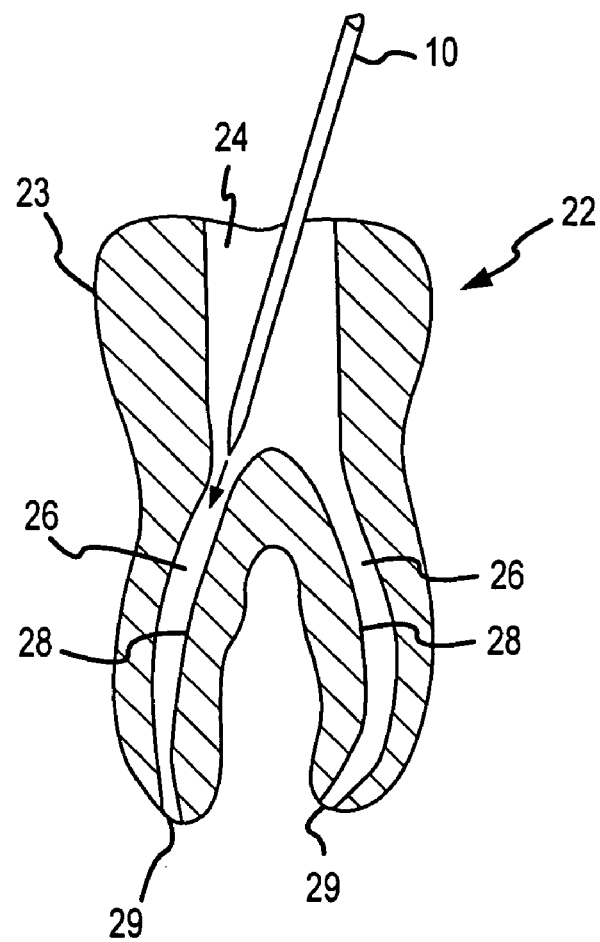
FIG. 2 is a cross sectional view of a tooth illustrating a step in a method for obturating a root canal using the plug of FIG. 1 according to an embodiment of the invention.

FIGS. 2 through 6 are cross sectional views of a tooth 22 that show the steps in a method for obturating a root canal 26 in the tooth 22 with a plug 10 according to an embodiment of the invention. In FIG. 2, the tooth 22 has been endodontically prepared for root canal obturation by first removing a portion of the crown 23 to form an access opening 24. The access opening 24 permits canal contents (not shown) to be removed from the tooth 22, and to expose the interior portions of the root canals 26. The root canals 26 are then commonly subjected to numerous mechanical shaping operations, including reaming or filing to obtain a root canal 26 with relatively long and slowly tapering walls 28. Prior to the introduction of obturation material into the canals 26, the canals 26 are regularly irrigated with cleaning or etching solutions to remove residual pulpal material and any dentin dislodged from the tooth 22 during the mechanical shaping of the canals 26.

Still referring to FIG. 2, the plug 10 is placed in the root canal 26 with the distal end 2 (as shown in FIG. 1) positioned adjacent to an apical foramen 29 of the tooth 22. The position of the plug 10 may be examined by radiographic techniques, such as x-ray imaging, to ensure that the plug 10 properly extends to the apical foramen 29. The plug 10 may be trimmed with scissors or softened with chloroform or other suitable solvents to conform to the contour of the canal 26. When it has been determined that the plug 10 is properly proportioned for the canal 26, and the canal 26 has been thoroughly dried, a light-curing adhesive may be applied to the walls 28 of the root canal 26, and the plug 10 is repositioned within the root canal 26. Alternatively, the light-curing adhesive may also be applied directly to the plug 10 prior to positioning the plug 10 into the root canal 26. The light-curing adhesive is a relatively low viscosity adhesive material that may be primarily composed of a blend of monomers, oligomers, and polymers containing the acrylate functionality, with photoinitiators having the appropriate light sensitivity added to the blend. Upon exposure to light of the proper intensity and spectral output, the photoinitiator in the adhesive decomposes to yield free radicals, which then initiate polymerization of the adhesive through the acrylate groups to create a thermoset polymer. The light-curing adhesive may have a viscosity in the range of at least about 0.5 centipoise (cP) to at least about 1.5 cP. An example of a suitable light-curing adhesive is the PRIME & BOND NT light-polymerizable dental adhesive available from the L. D. Caulk Division of Dentsply International, Inc. of York, Pa., although other alternatives may exist. The plug 10 may be subjected to a slight positioning force to ensure that the plug 10 is properly seated in the root canal 26.

Figure 3:
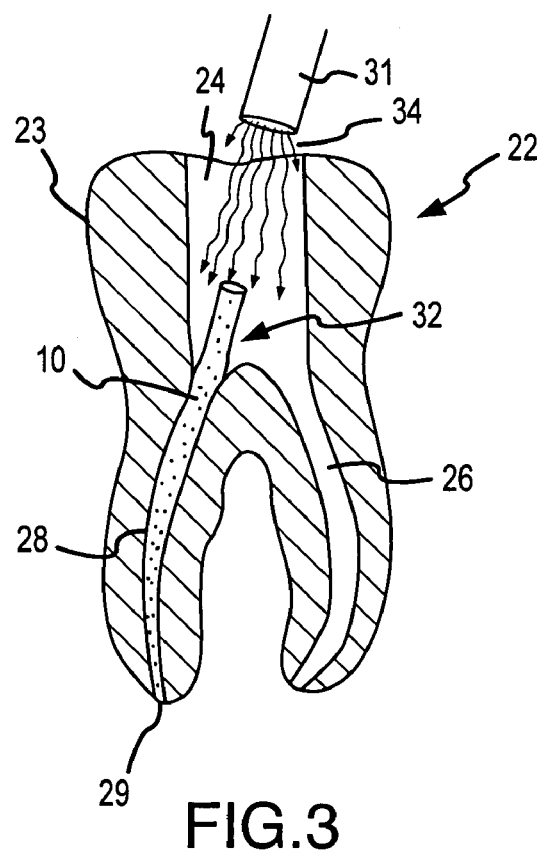
FIG. 3 is a cross sectional view of a tooth illustrating a step in a method for obturating a root canal using the plug of FIG. 1 according to an embodiment of the invention.

Turning now to FIG. 3, a light source 31 produces light 34 at a wavelength that activates the light-curing adhesive to bond the plug 10 to the walls 28 of the root canal 26. Since the plug 10 is comprised of a transparent or translucent material, the light 34 is transmitted through the material and along the length of the plug 10 to activate the light-curing adhesive interposed between the walls 28 of the root canal 26 and the plug 10. The plug 10 is thus positionally fixed and sealably secured by way of the light curing adhesive in the root canal 26. An example of a suitable light source 31 that is commonly employed by dentists is the SPECTRUM 800 curing light, which is available from the L. D. Caulk Division of Dentsply International, Inc. of York, Pa. Alternatively, the light source 31 may be comprised of other sources of illumination that provide light at various wavelengths, or a collimated light source such as a laser that is coupled to an optical fiber to transmit the light 34 to the upper portion 32 of the plug 10 may be used.

Figure 4:
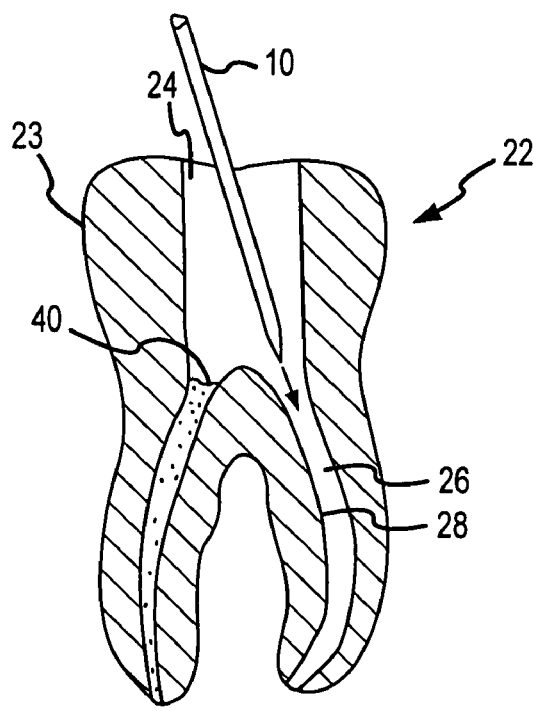
FIG. 4 is a cross sectional view of a tooth illustrating a step in a method for obturating a root canal using the plug of FIG. 1 according to another embodiment of the invention.

Still referring to FIG. 3, after the plug 10 has become positionally fixed and sealably secured in the canal 26, the upper portion 32 projecting upwardly from the plug 10 may be removed with a burr attached to a hand piece (not shown), or by thermally severing the upper portion 32 with a heated probe (also not shown), or by still other means to form a generally smooth terminal surface 40, at an upper end of the root canal 26, as shown in FIG. 4.

Figure 5:
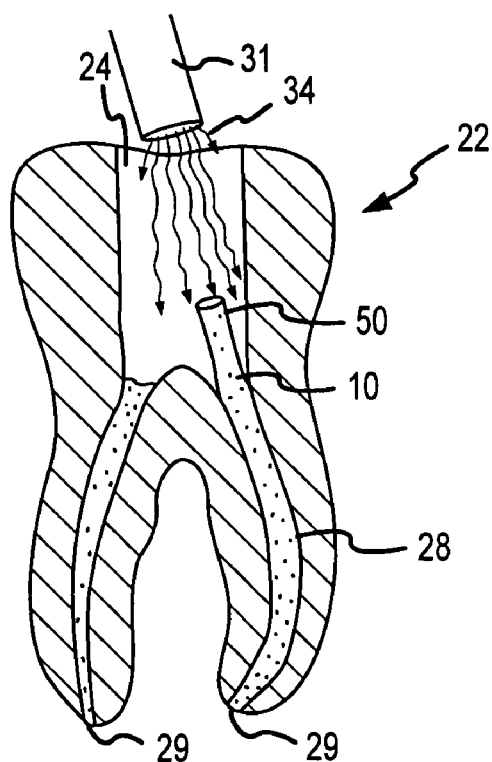
FIG. 5 is a cross sectional view of a tooth illustrating a step in a method for obturating a root canal using the plug of FIG. 1 according to another embodiment of the invention.
Figure 6:
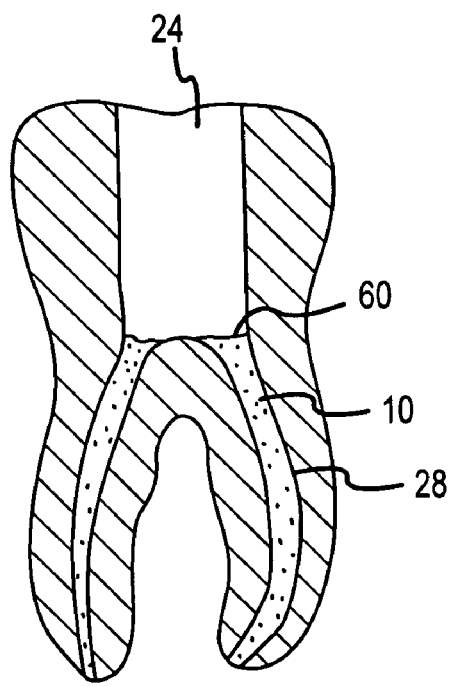
FIG. 6 is a cross sectional view of a tooth illustrating a step in a method for obturating a root canal using the plug of FIG. 1 according to another embodiment of the invention.

Referring to FIG. 4, additional root canals 26 present in the tooth 22 may be obturated by positioning a plug 10 into the canal 26 through the opening 24, as previously described. The plug 10 may then be positionally fixed and sealably secured to the wall 28 of the root canal 26 by exposing an upper portion 50 of the plug 10 to the light 34 to cure the adhesive, as shown in FIG. 5. The upper portion 50 may then be removed so that a smooth terminal surface 60 is formed, as shown in FIG. 6. An alternative approach that may be used to achieve the foregoing is to deposit the adhesive into each canal of the tooth having multiple canals, followed by placement of the plugs 10 into each canal. The plugs 10 may then be simultaneously exposed to the light 34 to seal all the canals 26 at the same time. In either case, following the obturation of all of the root canals 26 present in the tooth 22, the opening 24 may be restored by any conventional method presently used in dentistry.

In still another embodiment of the invention, the plug 10 and the adhesive compound may form complementary parts of a two-part bonding system. With reference still to FIGS. 1 through 6, the plug 10 may be comprised of a first component of the two-part system, while a relatively low viscosity second component that activates the bonding properties of the first component is applied to the wall 28 of the root canal 26. Since the bond between the plug 10 and the root canal surfaces is formed without the use of a light-curing bonding compound, it is not necessary to expose the plug 10 to a light source, as shown in FIGS. 3 and 5. For example, the first component may comprise a base component of the two part system, while the second portion comprises a catalyst portion. The first component may also comprise an activator that activates the bonding properties of the second component. In addition, a "dual cure" adhesive system that contains a photocatalyst to aid curing may also be used that would permit the plug 10 and the adhesive to cure chemically and by exposure to light. Although the "dual cure" system contains the photocatalyst, it is understood that the photocatalyst is included in the "dual cure" system to accelerate the curing process. Accordingly, the "dual cure" system will cure even in the absence of exposure to light, but the curing occurs at a slower rate. Accordingly, the "dual cure" system advantageously permits the plug 10 to bond to the root canal surfaces in cases where the light fails to reach all portions of the interface between the plug 10 and the root canal surfaces, or in cases where the light curing step is omitted entirely.

In yet another embodiment of the invention, the plug 10 may include a phosphorescent material capable of producing photoluminescence within the plug 10 after exposure of the plug 10 to an external source of light for a predetermined period of time. The photoluminescence of the plug 10 thus provides the light necessary to cure the previously-applied light-curing adhesive. Accordingly, the plug 10 may include various organic or inorganic compounds that are capable of phosphorescence. For example, various formulations comprised of anhydrous zinc sulfide and/or calcium tungstate may be used, which are commercially available as LUMI-LUX luminescent pigments from Allied Signal Specialty Chemicals, Inc. of Morristown, N.J. Since the photoluminescence produced by the phosphorescent material generally has a characteristic rate of decay after the external light source is removed, the photoluminescence must generally persist for a length of time that is sufficient to allow the plug 10 to be positioned within the root canal 26 after excitation of the luminescent material by the external light source, and to permit the light-curing bonding compound to be completely activated.

In yet still another embodiment of the invention, the plug 10 may include a radioisotope having a short half-life that activates a bonding compound distributed on the root canal wall 28 by exposing the bonding compound to alpha or beta decay, or through the emission of gamma radiation from the radioisotope in the plug 10.

The foregoing embodiments advantageously permit a root canal to be more reliably obturated than heretofore possible by using a relatively low viscosity adhesive material with the optically transmissive plug. Since the adhesive material is capable of migrating into lateral fissures and chemically bonding to the tooth and the plug material, a dentist will be able to produce a more reliable root canal obturation in generally less time than the prior-art gutta percha condensation methods currently require. Moreover, a dentist will be able to perform a root canal obturation in fewer steps with the foregoing embodiments than was heretofore possible. Thus, dentists with less general experience in root canal obturation will be able to routinely perform root canal obturations that have a higher probability of success than was previously obtainable. Still further, the disclosed method may be practiced with dental equipment that is commonly available in the dentist's office. For example, light-curing resins are commonly used in a variety of dental procedures so that suitable light sources to cure the resins are also generally present.

Figure 7:
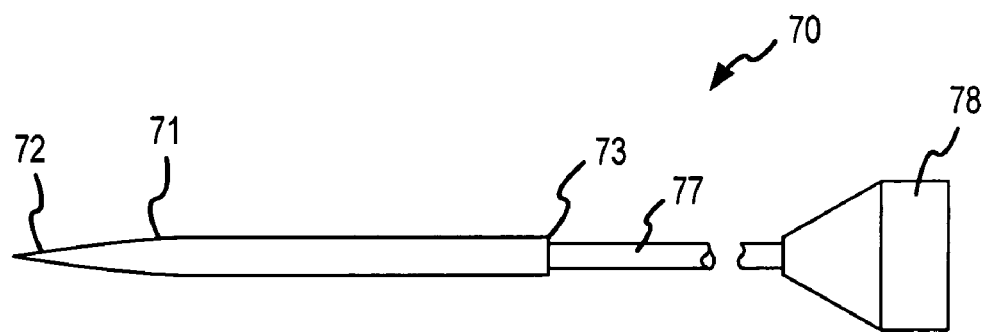
FIG. 7 is a plan view of a carrier for root canal obturation according to still another embodiment of the invention.

FIG. 7 is a plan view of a carrier 70 for root canal obturation according to still another embodiment of the invention. The carrier 70 includes a plug portion 71 having a distal end 72 and a proximal end 73 that may taper from the proximal end 73 towards the distal end 72 so that the plug portion 71 may be positioned within the generally tapered root canal of a tooth. The plug portion 71 may be formed from any optically transparent or translucent polymer suitable for biological implantation, which may include any of the materials previously identified in connection with other embodiments of the invention. The plug portion 71 further includes a central support portion 77 that is at least partially embedded in the plug portion 71, which extends from the plug portion 71 to a handle 78.

Figure 8:
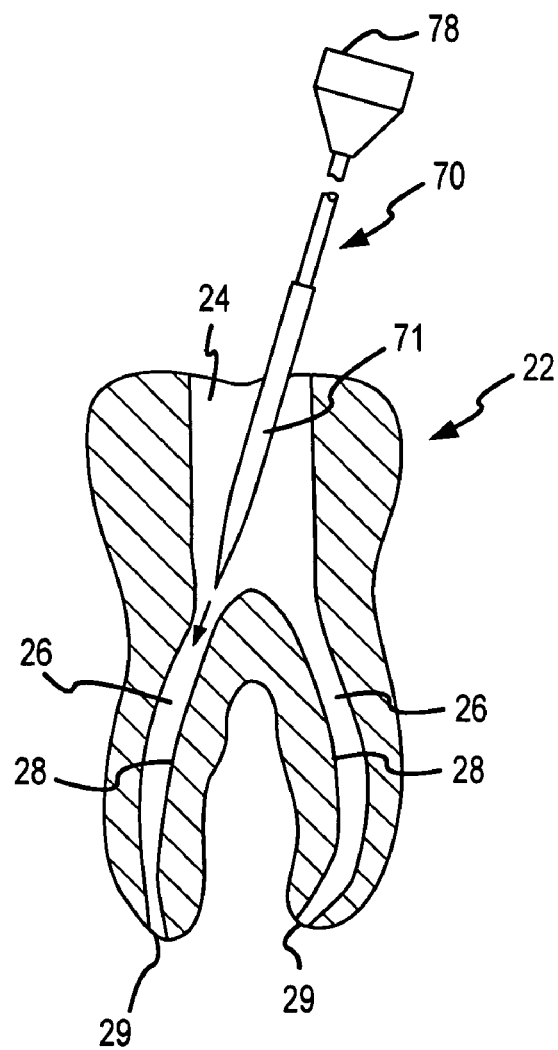
FIG. 8 is a cross sectional view of a tooth illustrating a step in a method for obturating a root canal using the carrier of FIG. 7 according to yet another embodiment of the invention.
Figure 9:
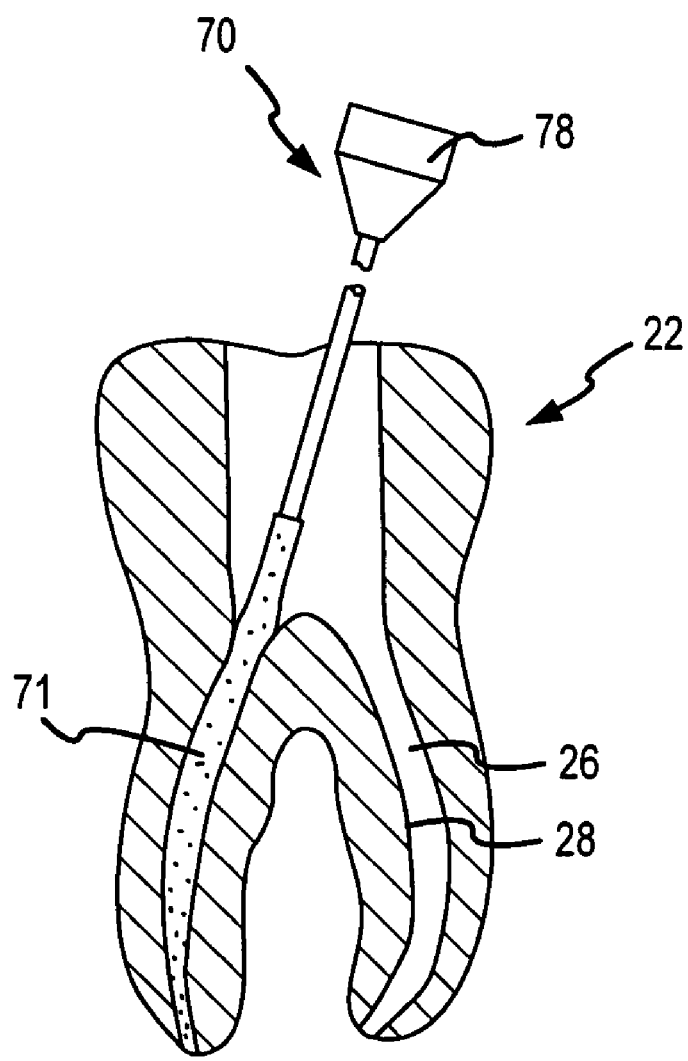
FIG. 9 is a cross sectional view of a tooth illustrating a step in a method for obturating a root canal using the carrier of FIG. 7 according to yet another embodiment of the invention.
Figure 10:
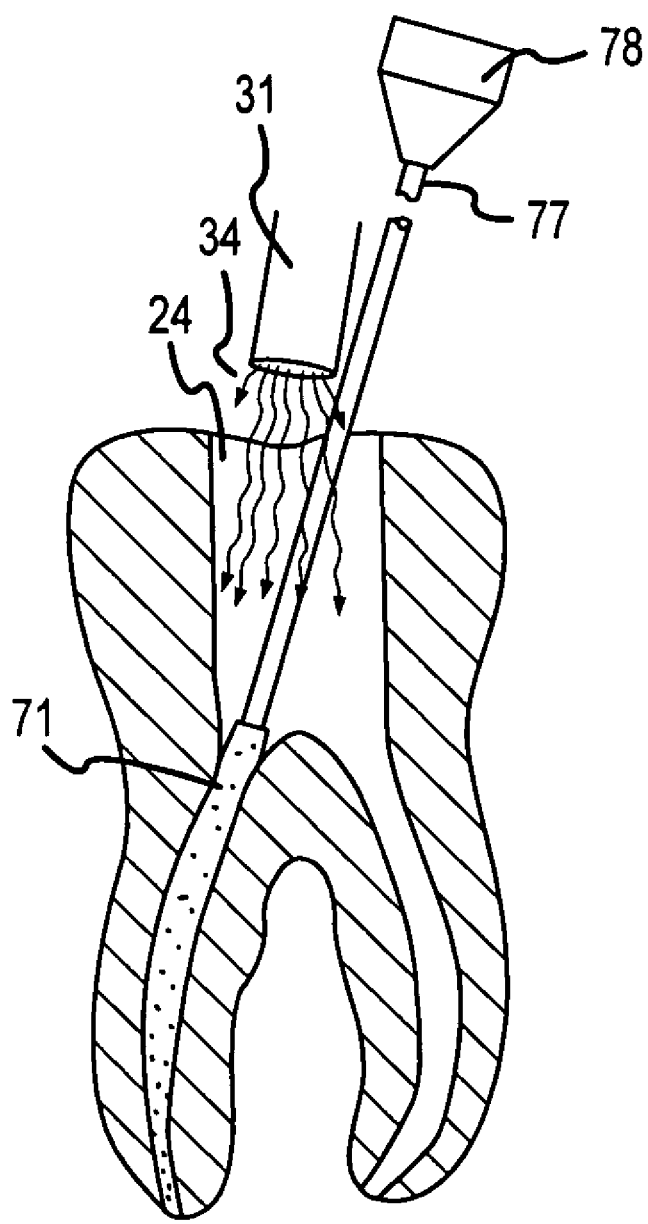
FIG. 10 is a cross sectional view of a tooth illustrating a step in a method for obturating a root canal using the carrier of FIG. 7 according to yet another embodiment of the invention.

FIGS. 8 through 10 are cross sectional views of a tooth 22 that show the steps in a method for obturating a root canal 26 in a tooth 22 with the carrier 70 according to another embodiment of the invention. For brevity, the following method will be described as applied to a single root canal. It is understood, however, that there may be more than a single root canal in a tooth, and that the method described below may be applied in succession to each of the root canals in the tooth. Referring now to FIG. 8, the plug portion 71 is introduced through the opening 24 and positioned in the root canal 26 by manual manipulation of the carrier 70. As previously described, the position of the plug portion 71 may be radiographically imaged to ensure that the plug portion 71 properly extends to the apical foramen 29 of the tooth 22. When it has been determined that the plug portion 71 is properly positioned in the canal 26, the plug portion 71 may be withdrawn from the canal 26, and a relatively low viscosity light-curing adhesive may then be applied to the walls 28 of the root canal 26. The light-curing adhesive may alternatively be applied directly to the plug portion 71 prior to positioning the plug portion 71 into the root canal 26. The knob 78 may be used to manipulate the carrier 70 and to apply slight positioning forces to the carrier 70 to properly seat the plug portion 71 in the root canal 26, as shown in FIG. 9. As previously described, the plug portion 71 may optionally be softened by heating the plug portion 71 with an external thermal source.

Figure 11:
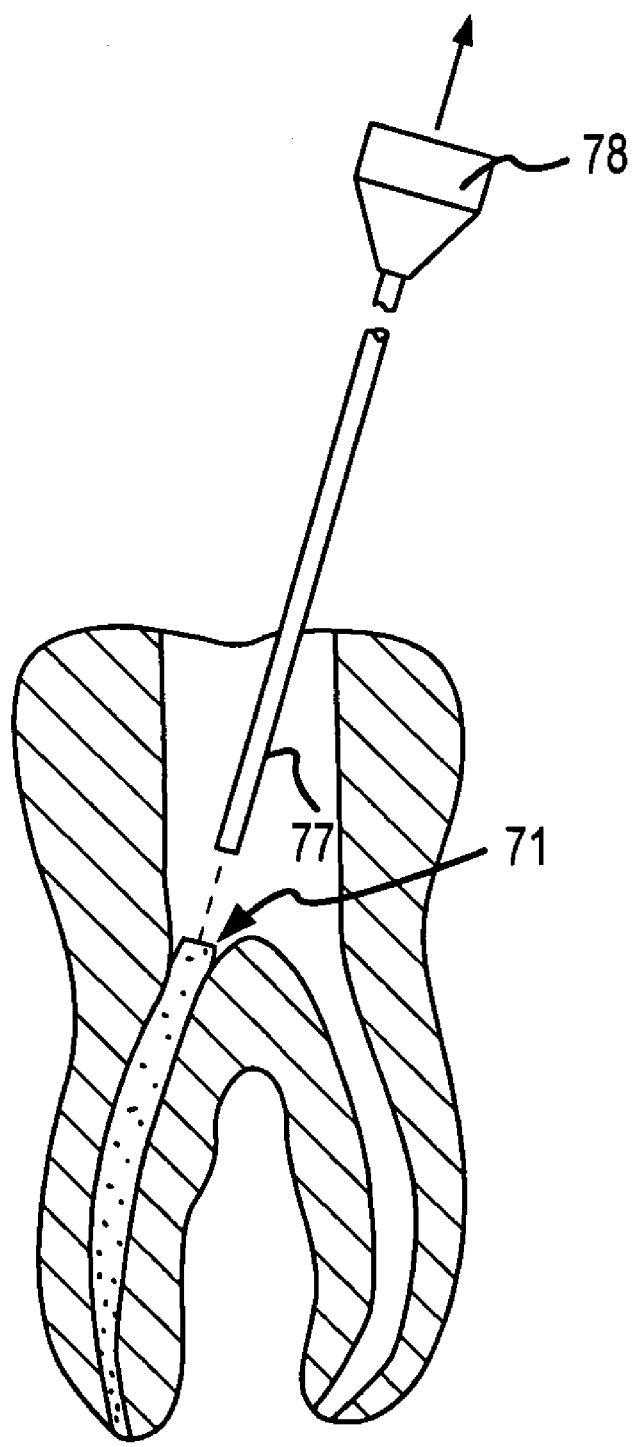
FIG. 11 is a cross sectional view of a tooth illustrating a step in a method for obturating a root canal using the carrier of FIG. 7 according to yet another embodiment of the invention.

Turning now to FIG. 10, the plug portion 71 of the carrier 70 may be exposed to light 34 from a light source 31 to provide illumination for activation of the light-curing adhesive. When the adhesive has been fully cured, the central support portion 77 and the handle 78 of the carrier 70 may be severed from the plug portion 71 using a burr mounted in a hand piece, or by other means, to leave the plug portion 71 positioned in the canal 26, as shown in FIG. 11.

Figure 12:
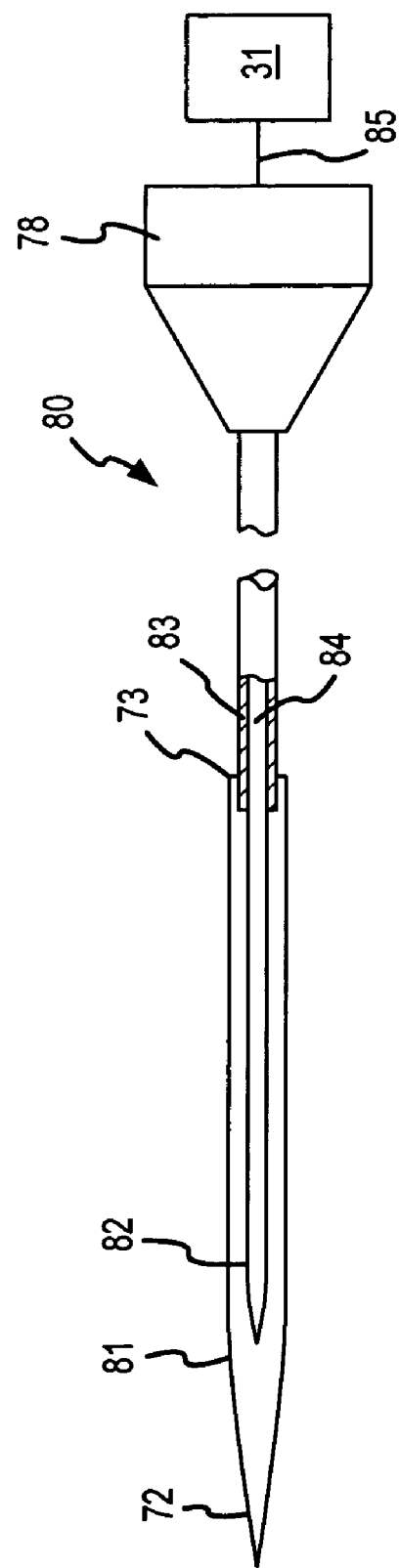
FIG. 12 is a plan view of a carrier for root canal obturation according to still yet another embodiment of the invention.

FIG. 12 is a plan view of a carrier 80 for root canal obturation according to still yet another embodiment of the invention. The carrier 80 includes a plug portion 81 having a distal end 72 and a proximal end 73 that may taper from the proximal end 73 towards the distal end 72 so that the plug portion 81 may be positioned within the generally tapered root canal of a tooth. The plug portion 81 may be formed from any optically transparent or translucent polymer, as discussed in connection with the previous embodiment. The plug portion 81 further includes an optical fiber 82 that extends from a handle 78 and along a central support portion 83 having an open interior 84 and into the plug portion 81. The optical fiber 82 is comprised of an optically transparent polymeric material having generally a higher rigidity than the material comprising the plug portion 81 so that the optical fiber 82 may act cooperatively with the central support portion 83 and the knob 78 to guide and properly position the plug portion 81 in the root canal of a tooth. An example of an optical fiber 82 that is suitable for use in this embodiment is the LUMILEEN polymethyl methacrylate (PMMA) optical fiber material available from PolyOptical, Inc. of Irvine Calif., although other suitable alternatives exist.

Still referring to FIG. 12, the carrier 80 may be coupled to a light source 31 through a fiber optic cable 85. The light source 31 may include an incandescent light source, although other sources of light may be used. For example, a coherent light source, such as a laser may also be used.

Figure 13:
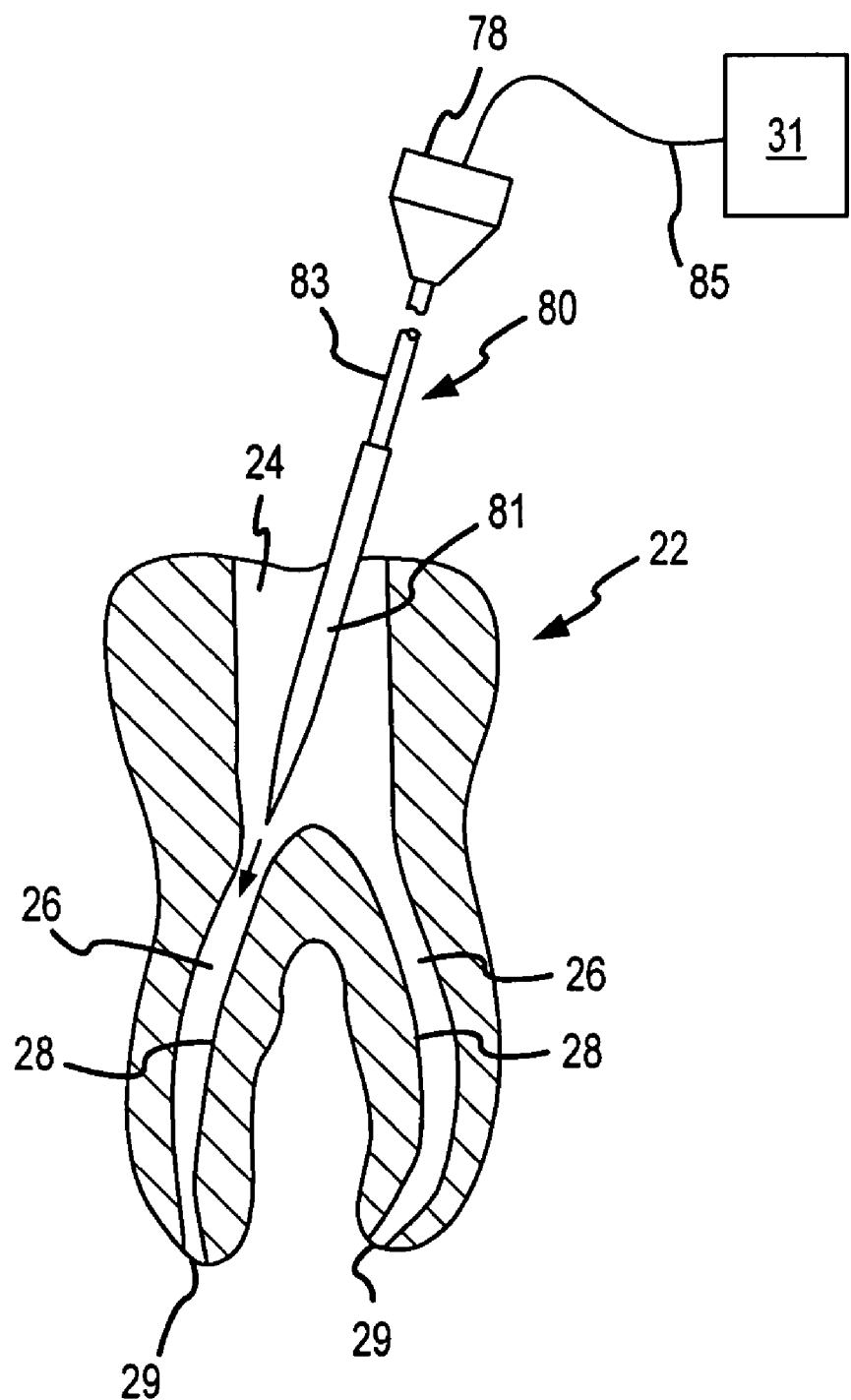
FIG. 13 is a cross sectional view of a tooth illustrating a step in a method for obturating a root canal using the carrier of FIG. 12 according to yet another embodiment of the invention.
Figure 14:
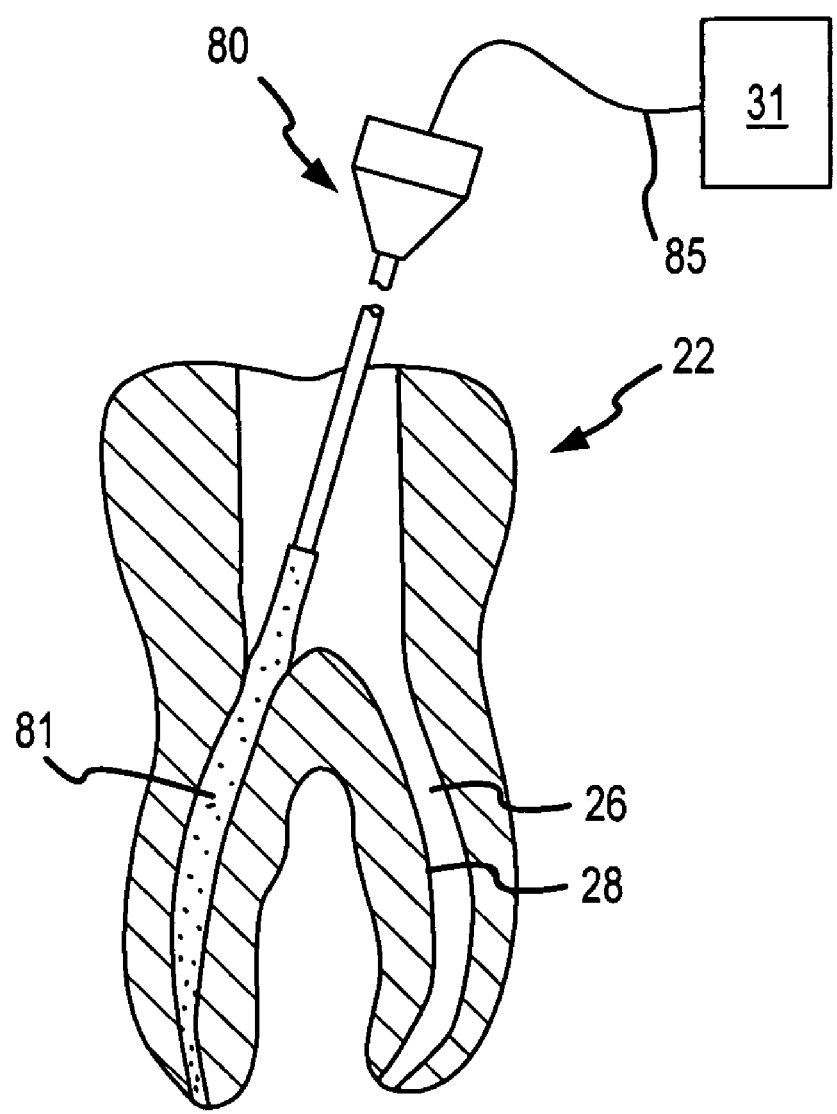
FIG. 14 is a cross sectional view of a tooth illustrating a step in a method for obturating a root canal using the carrier of FIG. 12 according to yet another embodiment of the invention.
Figure 15:
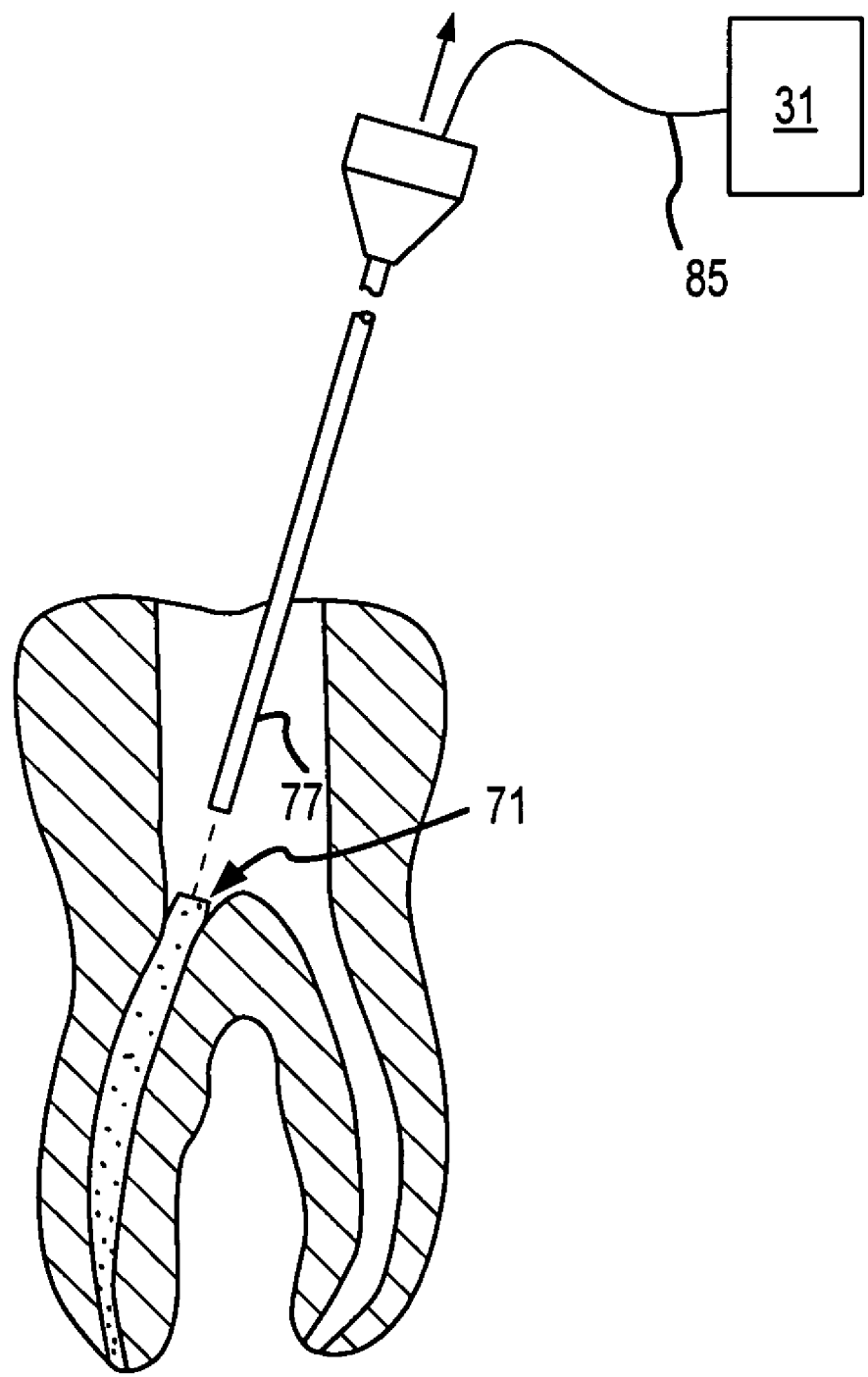
FIG. 15 is a cross sectional view of a tooth illustrating a step in a method for obturating a root canal using the carrier of FIG. 12 according to yet another embodiment of the invention.

FIGS. 13 through 15 are cross sectional views of a tooth 22 that show the steps in a method for obturating a root canal 26 in a tooth 22 with the carrier 80 according to still yet another embodiment of the invention. For brevity, the following method will be described as applied to a single root canal. Referring now to FIG. 13, the plug portion 81 is introduced through the opening 24 and positioned in the root canal 26 by manual manipulation of the carrier 80. As previously described, the position of the plug portion 81 may be radiographically imaged to ensure that the plug portion 81 properly extends to the apical foramen 29 of the tooth 22. When it has been determined that the plug portion 81 is properly positioned in the canal 26, the plug portion 81 may be withdrawn from the canal 26, and a relatively low viscosity light-curing adhesive may then be applied to the walls 28 of the root canal 26. The light-curing adhesive may alternatively be applied directly to the plug portion 81 prior to positioning the plug portion 81 into the root canal 26. The knob 78 may be used to manipulate the carrier 80 and to apply slight positioning forces to the carrier 80 to properly seat the plug portion 81 in the root canal 26. As previously described, the plug portion 81 may optionally be softened by heating the plug portion 81.

Turning now to FIG. 14, a light source 31 is activated to transmit light from the source 31 to the carrier 80 along a fiber optic cable 85. Light is then propagated along the optical fiber 82 (as shown in FIG. 12) and dispersed within the plug portion 81 to provide illumination for activation of the light-curing adhesive. The central support portion 83 and the handle 78 of the carrier 80 may then be severed from the plug portion 81 using a burr mounted in a hand piece, or by other means, as shown in FIG. 15.

In addition to the advantages described previously, the foregoing embodiments advantageously permit the plug portion to be more conveniently manipulated and positioned within the canal. Moreover, the fiber optic element positioned within the plug advantageously permits a greater and more uniform level of illumination to be achieved within the plug portion since the optical fiber extends relatively deeply into the root canal, which further assists the light-curing adhesive to cure.

Figure 16:
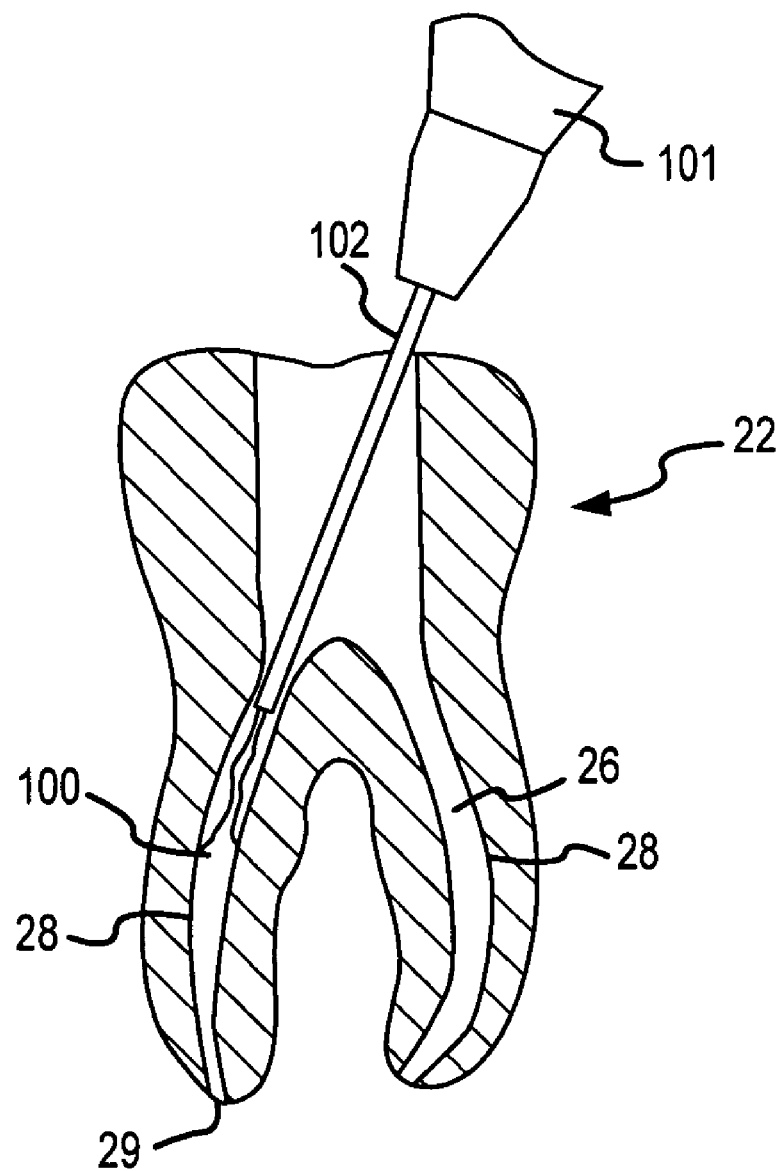
FIG. 16 is a cross sectional view of a tooth illustrating a step in a method for obturating a root canal according to an embodiment of the invention.
Figure 17:
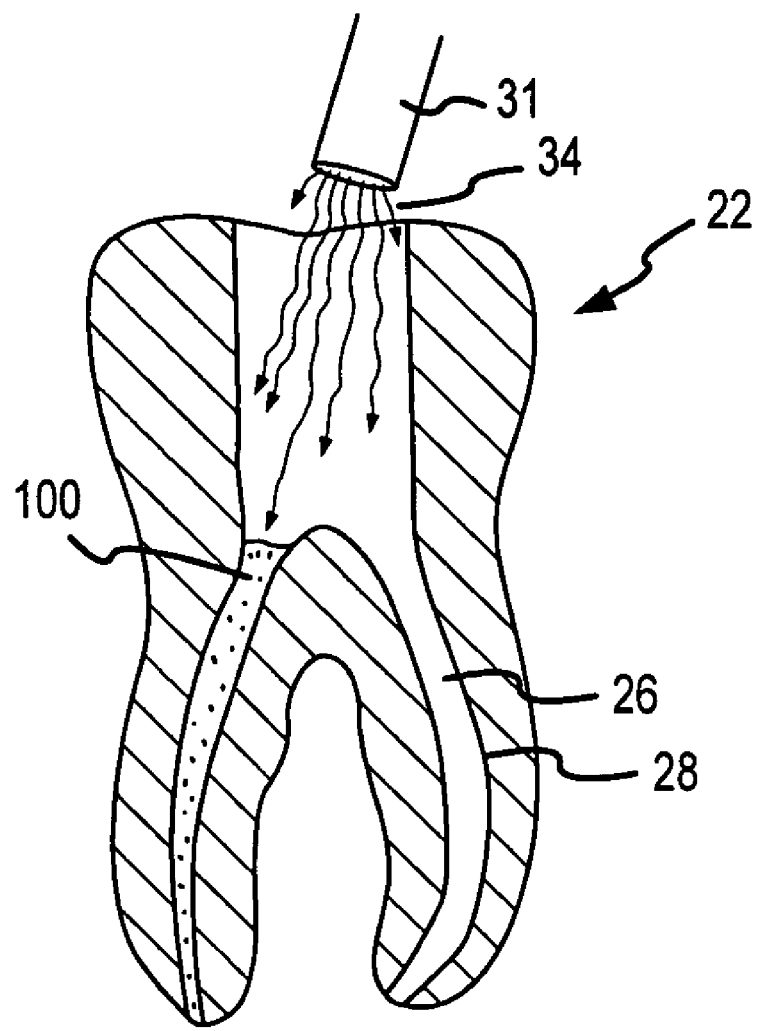
FIG. 17 is a cross sectional view of a tooth illustrating a step in a method for obturating a root canal according to an embodiment of the invention.

FIGS. 16 and 17 are cross sectional views of a tooth 22 that show the steps in a method for obturating a root canal in the tooth 22 according to still yet another embodiment of the invention. Referring now to FIG. 11, a filler material 100 is introduced into the root canal 26 in a semi-liquid form by a thermal heating device 101 that dispenses the filler material 100 through a filler tube 102 that is inserted through the opening 24 in the tooth 22. One suitable thermal heating device 100 is the Obtura II gutta percha gun, available from Spartan/Obtura, Inc. of Fenton, Mo. Prior to the introduction of the material into the canal 26, a relatively low viscosity light-curing adhesive is applied to the walls 28 of the root canal 26. The filler material 100 may be comprised of any optically transparent or translucent polymer suitable for biological implantation, which may include any of the materials previously identified in connection with other embodiments of the invention. The filler material 100 may be supplied to the thermal heating device 101 in a solid form, which may include particles or bead-like pellets of the material 100, in addition to other shapes. The material 100 is melted by the heat generated within the device 101 to form a flowable, plastic material 100 which may be also be pressurized by the device 101 so that the material 100 may be expelled from the device 101 through the filler tube 102 and into the root canal 26.

Turning now to FIG. 17, following the solidification of the material 100 within the root canal 26, light 34 emitted from a light source 31 may be introduced through the opening 24 to expose the material 100. The light 34 is transmitted along the length of the material 100 and activates the light-curing adhesive previously applied to the walls 28 of the root canal 26. The material 100 is thus adhesively fixed and sealably secured within the root canal 26.

The above description of illustrated embodiments of the invention is not intended to be exhaustive or to limit the invention to the precise form disclosed. While specific embodiments of, and examples of, the invention are described in the foregoing for illustrative purposes, various equivalent modifications are possible within the scope of the invention as those skilled within the relevant art will recognize. Moreover, the various embodiments described above can be combined to provide further embodiments. Accordingly, the invention is not limited by the disclosure, but instead the scope of the invention is to be determined entirely by the following claims.

The invention claimed is:

1. A plug for implantation into an endodontically prepared root canal of a tooth, comprising:
an elongated body comprised of a biologically compatible, resilient material comprised of a phosphorescent compound, the elongated body having a distal end and a proximal end and having a length to allow the distal end to be positioned adjacent to an apical portion of the tooth when the body is inserted in the root canal of the tooth, the body being further suitably provided in more than one predetermined configuration to permit the body to substantially abut the walls of the root canal of the tooth and extend to the apical portion of the root canal when implanted, the plug being further comprised of a material that is optically transmissive and fully polymerized prior to insertion into the root canal of the tooth.

2. The plug according to claim 1 wherein the optically transmissive material further comprises an optically transparent material.

3. The plug according to claim 1 wherein the optically transmissive material further comprises an optically translucent material.

4. The plug according to claim 1 wherein the elongated body further comprises an elongated body that tapers from the proximal end to the distal end.

5. The plug according to claim 1 wherein the material further comprises a material selected from the group consisting of silicones, polyethylenes, polyurethanes, polytetraflouroethylenes, polymethylmethacrylates (PMMA) and polytetraflourethyenes (PTFE).

6. The plug according to claim 1 wherein the material is further comprised of a radio-opacifier.

7. The plug according to claim 6 wherein the radio-opacifier is comprised of a barium compound.

8. The plug according to claim 6 wherein the radio-opacifier is comprised of a bismuth compound.

9. The plug according to claim 1 wherein the phosphorescent compound further comprises anhydrous zinc sulfide.

10. The plug according to claim 1 wherein the phosphorescent compound further comprises calcium tungstate.

11. The plug according to claim 1 wherein the material is further comprised of one component of a two component bonding system.

12. A plug for implantation into an endodontically prepared root canal of a tooth, comprising:
an elongated body comprised of a biologically compatible, resilient material comprised of a radioisotope having a relatively short half-life, the elongated body having a distal end and a proximal end and having a length to allow the distal end to be positioned adjacent to an apical portion of the tooth when the body is inserted in the root canal of the tooth, the body being further suitably provided in more than one predetermined configuration to permit the body to substantially abut the walls of the root canal of the tooth and extend to the apical portion of the root canal when implanted, the plug being further comprised of a material that is optically transmissive and fully polymerized prior to insertion into the root canal of the tooth.

13. A carrier for root canal obturation in an endodontically prepared tooth, comprising:
an elongated plug portion comprised of a biologically implantable, resilient material including a phosphorescent compound, the elongated plug portion having a distal end and a proximal end and having a length to allow the distal end to be positioned adjacent to an apical portion of the tooth when the plug portion is implanted in the root canal of the tooth, the distal end extending to the apical portion and substantially abutting the walls of the root canal when the plug is implanted, the plug portion being further configured in a plurality of predetermined and standardized shapes that are adapted conform to the contours of the root canal, and comprised of a material that is optically transmissive and fully polymerized prior to insertion into the root canal of the tooth; and
an elongated support portion having a first end coupled to the proximal end of the plug portion and an opposing second end.

14. The carrier according to claim 13 wherein the elongated plug portion is further comprised of an optically transparent material.

15. The carrier according to claim 13 wherein the elongated plug portion is further comprised of an optically translucent material.

16. The carrier according to claim 13 wherein the elongated plug portion further comprises an elongated plug portion that tapers from the proximal end to the distal end.

17. The carrier according to claim 13 wherein the elongated plug portion further comprises a radio-opacifier.

18. The carrier according to claim 13 wherein the elongated plug portion further comprises one component of a two component bonding system.

19. A carrier for root canal obturation in an endodontically prepared tooth, comprising:
an elongated plug portion comprised of a biologically implantable, resilient material including a radioisotope having a relatively short half-life, the elongated plug portion having a distal end and a proximal end and having a length to allow the distal end to be positioned adjacent to an apical portion of the tooth when the plug portion is implanted in the root canal of the tooth, the distal end extending to the apical portion and substantially abutting the walls of the root canal when the plug is implanted, the plug portion being further configured in a plurality of predetermined and standardized shapes that are adapted conform to the contours of the root canal, and comprised of a material that is optically transmissive and fully polymerized prior to insertion into the root canal of the tooth; and an elongated support portion having a first end coupled to the proximal end of the plug portion and an opposing second end.

20. The carrier according to claim 13 wherein the support portion further includes a handle positioned adjacent to the second end.

21. The carrier of claim 13, further comprising:
an optical fiber embedded in the plug portion that extends at least a partially along the length of the plug portion, the fiber further extending outwardly from the proximal end of the plug portion.

22. The carrier according to claim 21 wherein the support portion further includes an interior passage that extends from the first end to the second end, and the optical fiber extends along the interior passage.

23. A method for obturating a root canal passage in a tooth, comprising:
applying a light-curing adhesive to the root canal passage;
heating an optically transmissive plug to soften an exterior surface of the plug;
implanting the plug in the root canal passage having the plug being provided in more than one predetermined standardized configuration to permit the body to abut internal surfaces of the root canal passage and extend to an apical portion of the root canal when implanted, the plug being in a fully polymerized condition prior to implanting; and
exposing a portion of the plug to a light source to cure the adhesive.

24. The method according to claim 23 wherein applying a light-curing adhesive to the root canal passage further comprises applying a light-curing adhesive having a viscosity in the range of at least about 0.5 cP to at least about 1.5 cP.

25. The method according to claim 23 wherein exposing a portion of the plug to a light source further comprises exposing a portion of the plug to a source of light at a selected wavelength.

26. The method according to claim 23 wherein exposing a portion of the plug to a source of light is further comprised of exposing a portion of the plug to light through an optical fiber that is optically coupled to the light source.

27. The method according to claim 23 wherein implanting an optically transmissive plug into the root canal passage further comprises:
manipulating a carrier having an optically transmissive plug portion positioned on a support portion to place the plug portion in proximity to the root canal passage that extends to at least an apical portion of the root canal passage; and
inserting the plug portion into the root canal passage.

28. The method according to claim 27, further comprising severing the support portion from the plug portion.

29. A method for obturating a root canal passage in a tooth, comprising:
applying an adhesive to the root canal passage;
inserting an optically transmissive plug comprised of a phosphorescent material into the root canal passage, the plug being in a fully polymerized condition prior to inserting the plug into the root canal passage and extending to an apical portion of the root canal, the plug abutting internal surfaces of the root canal passage, the plug further being provided in more than one predetermined standardized configuration to permit the body to conform to a contour formed within the root canal passage by a corresponding endodontic rotary instrument; and
curing the adhesive by exposing the optically transmissive plug to a source of light to induce photoluminescence.

30. The method according to claim 29 wherein applying an adhesive to the root canal passage is further comprised of applying a first component of a two-part bonding system to the root canal passage; and inserting an optically transmissive plug into the root canal passage further comprises inserting a plug into the root canal passage that is formed from a second component of a two-part bonding system.

31. The method according to claim 29 wherein applying an adhesive to the root canal passage further comprises applying a light-curing adhesive to the root canal passage.

32. The method according to claim 31 wherein applying a light-curing adhesive further comprises applying a light-curing adhesive having a viscosity in the range of at least about 0.5 cP to at least about 1.5 cP.

33. A method for obturating a root canal passage in a tooth, comprising:
fusing an optically transmissive material to form a semi-liquid mass of the material;
applying a light-curing adhesive to the root canal passage;
injecting the semi-liquid mass into the root canal passage to form an obturating body within the root canal; and
exposing a portion of the obturating body to a light source to cure the adhesive.

34. The method according to claim 33 wherein applying a light-curing adhesive to the root canal passage further comprises applying a light-curing adhesive having a viscosity in the range of at least about 0.5 cP to at least about 1.5 cP.

35. The method according to claim 33 wherein exposing a portion of the obturating body to a light source further comprises exposing a portion of the body to a source of light at a selected wavelength.

36. The method according to claim 35 wherein exposing a portion of the obturating body to a source of light is further comprised of exposing a portion of the body to light through an optical fiber that is optically coupled to the light source.

37. The method according to claim 33 wherein fusing an optically transmissive material includes fusing an optically transmissive material in a "gutta percha gun."

38. An apparatus for endodontically treating a tooth, comprising:
an adhesive compound that includes a selected photocatalyst operable to promote polymerization of the compound upon exposure to light having a specified wavelength; and
a tapered plug configured to be implanted in a root canal of the tooth that is uniformly comprised of a flexible, resilient and optically transmissible polymeric material including a phosphorescent compound, the tapered plug corresponding to a taper formed in the root canal by a selected endodontic rotary instrument to permit the plug to occupy substantially an entire volume of the root canal when implanted so that a distal end of the plug extends at least proximate to an apical foramen of the root canal, the adhesive compound adapted to be interposed between the plug and an interior portion of the root canal to sealably secure the plug to the interior portion of the canal upon exposure to the light.

39. The apparatus of claim 38, wherein the optically transmissible material further comprises an optically transparent material.

40. The apparatus of claim 38, wherein the optically transmissible material further comprises an optically translucent material.

41. The apparatus of claim 38, wherein the adhesive compound further comprises a liquid having a viscosity of at least about 0.5 cP.

42. The apparatus of claim 38, wherein the adhesive compound includes a dual cure system.

43. The apparatus of claim 38, wherein the flexible and resilient material further comprises a material selected from a silicone, a polyethylene, a polyurethane, a polytetraflouroethylene, a polymethylmethacrylate (PMMA) and a polytetraflourethyene (PTFE).

44. The apparatus of claim 38, wherein the flexible and resilient material further comprises a radio-opacifier.

* * * * *